United States Patent
Kasuga et al.

(10) Patent No.: US 6,927,307 B2
(45) Date of Patent: Aug. 9, 2005

(54) METHOD FOR REACTIVATING CATALYST FOR METHACRYLIC ACID PREPARATION

(75) Inventors: Hiroto Kasuga, Himeji (JP); Eiichi Shiraishi, Himeji (JP)

(73) Assignee: Sumitomo Chemical Co., Ltd., Tokyo (JP)

( * ) Notice: Subject to any disclaimer, the term of this patent is extended or adjusted under 35 U.S.C. 154(b) by 0 days.

(21) Appl. No.: 10/649,817

(22) Filed: Aug. 28, 2003

(65) Prior Publication Data

US 2004/0044247 A1 Mar. 4, 2004

Related U.S. Application Data

(62) Division of application No. 09/956,896, filed on Sep. 21, 2001, now Pat. No. 6,664,206.

(30) Foreign Application Priority Data

Sep. 27, 2000 (JP) ........................................ 2000-294653

(51) Int. Cl.[7] .............................................. C07C 51/16
(52) U.S. Cl. ....................................... 562/532; 562/543
(58) Field of Search ............................... 502/20, 34, 55; 562/512, 598, 531, 532, 534, 535

(56) References Cited

U.S. PATENT DOCUMENTS

| | | | | | |
|---|---|---|---|---|---|
| 4,814,305 A | * | 3/1989 | Kamogawa et al. | ........... | 502/26 |
| 5,716,895 A | * | 2/1998 | Sugi et al. | ..................... | 502/24 |
| 6,664,206 B2 | * | 12/2003 | Kasuga et al. | ................ | 502/34 |
| 6,673,733 B2 | * | 1/2004 | Fukumoto et al. | ............ | 502/26 |
| 2002/0058582 A1 | * | 5/2002 | Kasuga et al. | ................ | 502/34 |

FOREIGN PATENT DOCUMENTS

JP 60232247 * 11/1985

* cited by examiner

*Primary Examiner*—Johann Richter
*Assistant Examiner*—Karl Puttlitz
(74) *Attorney, Agent, or Firm*—Sherman & Shalloway

(57) ABSTRACT

This invention provides a method of reactivating a catalyst for methacrylic acid production, which catalyst is used in production of methacrylic acid through vapor-phase oxidation of methacrolein or vapor-phase oxidative dehydrogenation of isobutyric acid, contains P and Mo, and exhibits reduced activity. The process comprises treating the catalyst, whose activity level has dropped (deteriorated catalyst), with a gas containing a nitrogen-containing heterocyclic compound (e.g., pyridine, piperidine, piperazine, quinoline).

5 Claims, No Drawings

METHOD FOR REACTIVATING CATALYST FOR METHACRYLIC ACID PREPARATION

CROSS REFERENCE TO RELATED APPLICATIONS

This application is a divisional of U.S. Ser. No. 09/956,896 filed Sep. 21, 2001, which issued as U.S. Pat. No. 6,664,206.

TECHNICAL FIELD TO WHICH THE INVENTION BELONGS

This invention relates to a method for reactivating a catalyst for methacrylic acid preparation. More particularly, the invention relates to a method for reactivating a catalyst which is used in the occasion of methacrylic acid preparation through vapor-phase oxidation of methacrolein or vapor-phase oxidative dehydrogenation of isobutyric acid and whose activity is lowered (which catalyst may hereafter be referred to as deteriorated catalyst).

PRIOR ART

Many proposals have been made in the past concerning catalysts useful for methacrylic acid preparation through vapor-phase oxidation of methacrolein or vapor-phase oxidative dehydrogenation of isobutyric acid.

However, it is invariably found difficult for all of those known catalysts to stably maintain the catalytic activity over a prolonged period. From economical standpoint, on the other hand, it is desirable to reactivate the deteriorated catalysts to allow their repetitive use.

Hence, methods of regenerating deteriorated catalysts have also been proposed: e.g., a method comprising, after withdrawing the deteriorated catalyst from reaction tubes, treating it with a nitrogen-containing heterocyclic compound (Patent Publication Hei 4 (1992)-50062B1-JP) and a method comprising, after withdrawing the deteriorated catalyst from reaction tubes, treating it with aqueous ammonia and a nitrogen-containing heterocyclic compound, (Patent Publication Hei 7 (1995)-20552B1-JP) and the like. Those methods, however, consist of many steps such as (1) withdrawing the deteriorated catalyst from reaction tubes, (2) treating it in an aqueous medium, (3) if necessary, drying the treated catalyst, (4) shaping the resultant solid and (5) calcining the same, and hence cannot be regarded as industrially advantageous methods.

On the other hand, methods of reactivating the deteriorated catalyst within the reaction tubes have also been proposed, including: a method of treating the deteriorated catalyst with ammonia and water (Patent Publication Sho 54 (1979)-11272B1-JP); a method of treating with a nitrogen-containing compound such as nitric acid and nitrous acid (Patent Publication Sho 56 (1981)-91846A-JP); a method of treating with a gas containing at least 10 vol. % of steam (Patent Publication Sho 58 (1983)-156351A-JP); and a method of treating with a gas containing at least 0.2 vol. % of oxygen (patent Publication Hei 6 (1994)-7685A-JP). According to these methods, however, not necessarily satisfactory results are guaranteed, although the treated, deteriorated catalysts do recover their activity to a certain extent.

PROBLEMS TO BE SOLVED BY THE INVENTION

The object of the present invention is to provide a method for efficiently reactivating a catalyst which is used in the occasion of methacrylic acid preparation through catalytic vapor-phase oxidation of methacrolein or catalytic vapor-phase oxidative dehydrogenation of isobutyric acid, which contains P and Mo, and whose activity level has dropped.

MEANS TO SOLVE THE PROBLEM

Our extensive studies have found that such deteriorated catalysts could be effectively regenerated by treating them with a gas containing a nitrogen-containing heterocyclic compound. We have also discovered that the deteriorated catalysts could be very effectively regenerated, when they are treated with a gas which contains a nitrogen-containing heterocyclic compound and steam; or with a gas which contains a nitrogen-containing heterocyclic compound and another gas which contains steam. That is, we have discovered that the catalysts which were reactivated (hereafter referred to as reactivated catalysts) with a gas which contained a nitrogen-containing heterocyclic compound restored the activity level approximately equivalent to the original level and furthermore maintained the restored activity level stably over a prolonged term. This invention is completed based on those discoveries.

According to the present invention, therefore, a method of reactivating a catalyst for methacrylic acid production is provided, said catalyst being used in the occasions of producing methacrylic acid through vapor-phase oxidation of methacrolein or vapor-phase oxidative dehydrogenation of isobutyric acid, containing P and Mo and exhibiting reduced catalytic activity, which method is characterized by treating the catalyst with a gas which contains a nitrogen-containing heterocyclic compound.

According to the invention, furthermore, a method for reactivating a catalyst for methacrylic acid production is provided, said catalyst being used in the occasions of producing methacrylic acid through vapor-phase oxidation of methacrolein or vapor-phase oxidative dehydrogenation of isobutyric acid, containing P and Mo and exhibiting reduced catalytic activity, which method is characterized by treating the catalyst with a gas which contains a nitrogen-containing heterocyclic compound and steam; or with a gas which contains a nitrogen-containing heterocyclic compound and another gas which contains steam.

EMBODIMENTS OF THE INVENTION

Kind of the catalysts for methacrylic acid production, which are the objects of the reactivation method of the present invention, is not critical, so long as they are useful in the occasions of producing methacrylic acid through vapor-phase oxidation of methacrolein or vapor-phase oxidative dehydrogenation of isobutyric acid, and contain P and Mo. More specifically, heteropolyacid catalysts containing heteropolyacids having P—Mo or P—Mo—V as their essential constituents, or salts thereof may be named. In particular, the method of the invention is conveniently used for reactivating the heteropolyacid catalysts which are expressed by the following general formula (1):

$$P_a Mo_b V_c X_d Y_e O_f \qquad (1)$$

(wherein Mo, V, P and O are molybdenum, vanadium, phosphorus and oxygen, respectively; X stands for at least one element selected from the group consisting of potassium, rubidium, cesium and thallium; Y is at least an element selected from the group consisting of alkaline earth metals, copper, silver, arsenic, antimony, bismuth, iron, cobalt, nickel, chromium, manganese, tungsten, zirconium, niobium, titanium, zinc, tin, selenium, tellurium, germanium, palladium, rhodium, rare earth elements and silicon; and suffixes a, b, c, d, e and f denote atomic ratios of the respective elements, where when b is 12, a, c, d and e each is a value not more than 3 but not including 0 (zero), and f is a value determined by valencies and atomic ratios of those elements other than oxygen).

Those heteropolyacid catalysts which are expressed by the general formula (1) are known per se, and can be prepared by themselves accepted methods.

The reactivation method of the invention is used for regenerating above-described catalysts for methacrylic acid production, which are deteriorated for various reasons. Specific examples of the deteriorated catalysts include those whose activity level dropped because of exposure to high temperatures not lower than 450° C. for many hours under temperature control failure during the reaction; because of use in the reaction for a prolonged period while oxygen or methacrolein supply is suspended; or because of temperature control failure during the catalyst calcination, in consequence exposing the catalyst under preparation to high temperatures; those whose activity level gradually dropped during the continuous reaction over a long term; or those which are given a high temperature oxidation treatment for removing polymers deposited on the catalyst surface. In particular, the reactivation method of the invention is conveniently used for regeneration of the catalysts whose activity is gradually reduced during the continuous reaction over a prolonged term.

The nitrogen-containing heterocyclic compound to be used in the invention is subject to no critical limitation, and can be suitably selected from known nitrogen-containing heterocyclic compounds. In particular, at least one compound selected from pyridine, piperidine, piperazine, quinoline and derivatives thereof is conveniently used.

The concentration of the nitrogen-containing heterocyclic compound in the gas used in the reactivation treatment, (which is hereinafter referred to as the regeneration gas) is not critical. Whereas, normally it ranges from 0.01 to 50 volume %, preferably 0.05–30 volume %, inter alia, 0.1–10 volume %. Where it is lower than 0.01 volume %, economically and industrially undesirable results are invited such as that the treating time needs to be increased for achieving the intended effect or the flow rate of the regeneration gas must be increased. On the other hand, the concentration higher than 50 volume % cannot achieve the correspondingly favorable effect, resulting in waste of the nitrogen-containing heterocyclic compound and is ineconomical.

The regeneration gas according to the invention may contain, in addition to said nitrogen-containing heterocyclic compound, steam and/or ammonia and/or aliphatic amine and the like. Such steam and/or ammonia and/or aliphatic amine and the like may be passed simultaneously with, or separately from, said nitrogen-containing heterocyclic compound. When they are passed separately, their order of flowing is not critical. Where these steam and/or ammonia and/or aliphatic amine and the like are used, their concentrations in the regeneration gas are 0.01 to 50 volume %, preferably 0.05–30 volume %, inter alia, 0.1–10 volume % for each of them. Constituent(s) of the rest of the regeneration gas is not critical, while nitrogen or air, or their gaseous mixtures are recommendable for economical reasons.

For example, when steam is to be concurrently used, the deteriorated catalyst can be treated with ① a gas containing steam and a nitrogen-containing heterocyclic compound, or ② separately with a gas containing a nitrogen-containing heterocyclic compound and a steam-containing gas. In the latter case, the treatment with the steam-containing gas may be conducted either before or after that with the gas which contains a nitrogen-containing heterocyclic compound. Concurrent use of steam in that manner enables still more effective regeneration of those deteriorated catalysts.

It is sufficient for the treating temperature to be of the level not liquefying such components as the nitrogen-containing heterocyclic compound and steam in the regeneration gas. When it exceeds 500° C., decomposition of heteropolyacid in the catalyst is induced, which is undesirable. Normally the treatment can be conducted at temperatures not higher than 300° C., preferably not higher than 200° C.

The treating time and flow rate of the regeneration gas can be suitably determined depending on the extent of deterioration of the catalyst to be treated and the composition of the regeneration gas.

The reactivation of the deteriorated catalyst can be performed after withdrawing the catalyst from reaction tubes, but in situ reactivation in the reaction tubes is simpler in operation and economically advantageous. Where the reactivation is conducted in the reaction tubes, the direction of passing the regeneration gas may be the same or opposite to that of the reactant gas in the oxidation or oxidative dehydrogenation reaction, or it may be reversed during the regeneration treatment.

In the reactivation treatment of the invention, it is recommendable to conduct a heating treatment at 100–500° C., preferably 100–450° C., after the above-described treatment with a regeneration gas. More specifically, after the treatment with a regeneration gas, the catalyst is preferably treated at 100–450° C., under introduction of an inert gas such as gaseous nitrogen, and then calcined in air at 200–450° C.

The catalytic vapor-phase oxidation or oxidative dehydrogenation reaction involved in the present invention is performed by introducing a gaseous mixture of 1–10 volume % of a starting material (methacrolein or isobutyric acid), 1–10 volume times thereof of molecular oxygen and inert gas serving as a diluent, onto the catalyst at a temperature within a range of 200–400° C., at a pressure in a range of 0.1–1 MPa and at a space velocity in a range of 100–5,000 $h^{-1}$ (STP). Examples of useful inert gas include nitrogen, carbon dioxide, steam and the like. In particular, use of steam is advantageous for improving yield of the object product, because it has the action to inhibit formation of side products.

Starting methacrolein or isobutyric acid are not necessarily pure. Where the starting material is methacrolein, a methacrolein-containing gas derived from catalytic vapor-phase oxidation of isobutylene or tertiary butanol may be used, which is particularly recommendable for industrial processes.

[Effect of the Invention]

According to the method of the invention, deteriorated catalysts can be readily reactivated with high efficiency. Those reactivated catalysts obtained by the method of the invention exhibit equivalent catalytic activity to that of the fresh catalysts and furthermore maintain said activity level stably over a prolonged period. Accordingly, by alternatively repeating vapor-phase oxidation of methacrolein or vapor-phase oxidative dehydrogenation of isobutyric acid, and the reactivation of the deteriorated catalyst according to the present invention, methacrylic acid can be stably produced over a prolonged period.

EXAMPLES

Hereinafter the invention is explained more specifically, referring to working Examples, wherein the conversion and selectivity have the following definitions.

$$\text{Conversion (mol \%)} = \left(\frac{\text{mol number of reacted starting material}}{\text{mol number of supplied starting material}}\right) \times 100$$

$$\text{Selectivity (mol \%)} = \left(\frac{\text{mol number of formed methacrylic acid}}{\text{mol number of reacted starting material}}\right) \times 100$$

The performance test of each catalyst and deterioration-accelerating test were conducted in the following manner.
<Performance Test>
Fifty (50) ml of a catalyst was charged in a U-shaped stainless steel tube of 25 mm in inner diameter, and the tube was immersed in a 280° C. molten salt bath. Through said tube a starting gaseous mixture of methacrolein:oxygen:nitrogen:water=1:3:36:10 by volume ratio was passed at a space velocity of 1,000 h$^{-1}$ (STP).
<Deterioration-Accelerating Test>
Fifty (50) ml of a catalyst was filled in a stainless steel reaction tube of 25 mm in inner diameter. The tube was immersed in a molten salt bath of 350° C., and through which a starting gaseous mixture of methacrolein:oxygen:nitrogen:water=1:3:36:10 by volume ratio was passed at a space velocity of 2,000 h$^{-1}$ (STP) continuously for 1,000 hours or 2,000 hours.

Referential Example 1

[Catalyst Preparation]

To 2,800 ml of 60° C. water, 1,236 g of ammonium paramolybdate and 68.2 g of ammonium matavanadate were dissolved and stirred, followed by further addition of 280 g of pyridine and 87.4 g of phosphoric acid (85 wt. %), and a solution of 770 g of nitric acid (65 wt. %), 136.4 g of cesium nitrate and 14.1 g of copper nitrate as dissolved in 1,000 ml of water, by the order stated. This aqueous mixture was concentrated under heating and stirring, and the resulting clay-like substance was molded into columns of each 5 mm in diameter and 6 mm in height, which were dried at 250° C. and calcined in a gaseous nitrogen stream at 430° C. for 4 hours, and then in an air stream at 400° C. for 2 hours. The composition of so obtained catalyst was as follows, in terms of atomic ratios of the metal elements excluding oxygen, P:Mo:V:Cu:Cs=1.3:12:1:0.1:1.2. Upon X-ray diffraction (per cathode Cu—Kα) measurement, the catalyst was found to be composed mainly of molybdovanadophosphoric acid and its partial metal salt. The result of the catalytic performance test of thus obtained fresh catalyst 1 was as shown in Table 1.

[Deterioration of the Catalyst]

Deteriorated catalyst 1 was obtained by subjecting above fresh catalyst 1 to the deterioration-accelerating test continuously for 1,000 hours. Also by subjecting the same catalyst to the deterioration-accelerating test continuously for 2,000 hours, deteriorated catalyst 2 was obtained. The result of the catalytic performance test given to these deteriorated catalysts 1 and 2 was as shown in Table 1.

Referential Example 2

[Catalyst Preparation]

A fresh catalyst 2 was prepared by repeating the catalyst preparation procedures of Referential Example 1, except that the addition of 280 g of pyridine was omitted.

[Catalyst Deterioration]

The fresh catalyst 2 was subjected to the deterioration-accelerating test continuously for 1,000 hours, to provide deteriorated catalyst 3.

Example 1

[Reactivation Treatment-1]

Deteriorated catalyst 1 was not withdrawn from the reaction tube, and the molten salt bath temperature was dropped to room temperature while passing a gaseous current of nitrogen through the reaction tube. Thereafter a gas composed of 1 volume % of pyridine and the balance of nitrogen was passed for 3 hours at 30° C. and at a space velocity of 1,000 h$^{-1}$. The pyridine supply then was stopped and nitrogen alone was passed during the subsequent 10 hours during which the temperature was raised to 430° C., following 4 hours' retention of said temperature and the temperature drop to 400° C. Thereafter nitrogen was switched to air for the following 2 hours' temperature retention, and then switched back to nitrogen during the temperature drop to 280° C. Whereupon reactivated catalyst 1 was obtained. The result of the catalytic performance test of this reactivated catalyst 1 was as shown in Table 2.

[Deterioration of Catalyst]

The reactivated catalyst 1 was subjected to the deterioration-accelerating test continuously for 1,000 hours to provide deteriorated catalyst 4. The result of the catalytic performance test was as shown in Table 2.

[Reactivation Treatment-2]

Deteriorated catalyst-4 was treated in the same manner as the reactivation treatment-1, to provide reactivated catalyst 2. The result of the catalytic performance test of the reactivated catalyst 2 was as shown in Table 2.

[Deterioration of Catalyst]

The reactivated catalyst 2 was subjected to the deterioration-accelerating test continuously for 1,000 hours, to provide deteriorated catalyst 5. The result of its catalytic performance test was as shown in Table 2.

The results of the catalytic performance test of deteriorated catalysts 4 and 5 show that the reactivated catalysts 1 and 2 stably maintained their catalytic performance over a prolonged period, to the extent equivalent to the fresh catalyst.

Comparative Example 1

In the reactivation treatment-1 of Example 1, the molten bath temperature was dropped to room temperature, and thereafter gaseous nitrogen alone was passed through the reaction tube for 3 hours at 30° C. and at a space velocity of 1,000 h$^{-1}$, without using any pyridine and not followed by the heat treatment. So treated catalyst was subjected to the catalytic performance test, with the result as shown in Table 2.

Comparative Example 2

The reactivation treatment-1 of Example 1 was repeated except that no pyridine was used. The catalytic performance test result of so treated catalyst was as shown in Table 2.

Comparative Example 3

The reactivation treatment-1 of Example 1 was repeated except that the pyridine was replaced with 1 volume % of water. The catalytic performance test result of so treated catalyst was as shown in Table 2.

Examples 2–11

The reactivation treatment-1 of Example 1 was repeated except that the treating conditions were varied for each run as shown in Table 3. The results of the catalytic performance test of so obtained reactivated catalysts were as shown in Table 3.

Examples 12–15

The reactivation treatment-1 of Example 1 was repeated except that the pyridine gas was replaced with another gas for each run as indicated in Table 3. The results of the catalytic performance test of so obtained reactivated catalysts were as shown in Table 3.

Example 16

The reactivation treatment-1 of Example 1 was repeated except that a gas composed of 1 volume % of steam and the balance of nitrogen was passed through the reaction tube at 30° C. and at a space velocity of 1,000 h$^{-1}$ for additional 3 hours after the treatment with the pyridine gas. The result of the catalytic performance test of so obtained reactivated catalyst was as shown in Table 3.

Example 17

The reactivation treatment-1 of Example 1 was repeated except that the gas composed of 1 volume % of steam and the balance of nitrogen was passed through the reaction tube at 30° C. and at a space velocity of 1,000 h$^{-1}$ for 3 hours, in advance of the treatment with the pyridine gas. The result of the catalytic performance test of so obtained reactivated catalyst was as shown in Table 3.

Example 18

Deteriorated catalyst 3 was reactivated by the reactivation treatment-1 as described in Example 1. The resulting reactivated catalyst was given the catalytic performance test, showing a methacrolein conversion of 74.8 mol % and a methacrylic acid selectivity of 75.9 mol %.

TABLE 1

| | | Deterioration-accelerating reaction time (hrs.) | Methacrolein conversion (mol %) | Methacrylic acid selectivity (mol %) |
|---|---|---|---|---|
| Referential Example 1 | fresh catalyst 1 | | 88.7 | 88.3 |
| | deteriorated catalyst 1 | 1000 | 76.3 | 87.9 |
| | deteriorated catalyst 2 | 2000 | 67.4 | 89.1 |
| Referential Example 2 | fresh catalyst 2 | | 80.5 | 75.3 |
| | deteriorated catalyst 3 | 1000 | 65.3 | 76.4 |

TABLE 2

| | | | Methacrolein conversion (mol %) | Methacrylic acid selectivity (mol %) |
|---|---|---|---|---|
| Example 1 | after reactivation treatment | reactivated catalyst 1 | 84.4 | 88.1 |
| | after deterioration-accelerating test | deteriorated catalyst 4 | 73.1 | 87.8 |
| | after reactivation treatment | reactivated catalyst 2 | 78.8 | 88.0 |
| | after deterioration accelerating test | deteriorated catalyst 5 | 67.1 | 89.1 |
| Comparative Example 1 | no treatment | | 76.3 | 87.9 |
| | after deterioration-accelerating test | | 67.7 | 88.5 |
| Comparative Example 2 | heat treatment alone | | 77.1 | 88.2 |
| | after deterioration-accelerating test | | 68.0 | 88.7 |
| Comparative Example 3 | water treatment | | 78.1 | 82.3 |
| | after deterioration-accelerating test | | 67.2 | 83.4 |

TABLE 3

| | Treating conditions | Methacrolein conversion (mol %) | Methacrylic acid selectivity (mol %) |
|---|---|---|---|
| Example 2 | treating temperature 80° C. | 84.1 | 88.2 |
| Example 3 | treating temperature 150° C. | 84.2 | 88.1 |
| Example 4 | pyridine concentration 0.1 vol % | 81.4 | 88.0 |
| Example 5 | pyridine concentration 5.0 vol % | 83.9 | 87.9 |
| Example 6 | pyridine concentration 10 vol % | 84.0 | 88.3 |
| Example 7 | treated outside the reaction tube | 84.2 | 88.4 |
| Example 8 | nitrogen changed to air | 83.8 | 88.0 |
| Example 9 | SV 100 h$^{-1}$ | 80.9 | 88.3 |
| Example 10 | SV 100 h$^{-1}$ treating time tenfold | 84.2 | 87.9 |
| Example 11 | SV 10000 h$^{-1}$ | 84.0 | 88.1 |
| Example 12 | pyridine 1 vol. % + steam 1 vol. % | 85.5 | 87.8 |
| Example 13 | pyridine 1 vol. % + ammonia 1 vol. % + steam 1 vol. % | 85.6 | 88.1 |
| Example 14 | piperidine 1 vol. % | 84.0 | 87.9 |
| Example 15 | quinoline 1 vol. % | 83.9 | 87.9 |
| Example 16 | steam treatment after pyridine treatment | 85.7 | 88.4 |
| Example 17 | pyridine treatment after steam treatment | 85.2 | 88.0 |

What is claimed is:

1. A process for producing methacrylic acid through catalytic vapor-phase oxidation of methacrolein or catalytic vapor-phase oxidative dehydrogenation of isobutyric acid, characterized by using a catalyst which has been reactivated by method comprising treating a catalyst which has been gradually deteriorated during a long-term continuous reaction operation for use in methacrylic acid production by vapor-phase oxidation of methacrolein or vapor-phase oxidative dehydrogenation of isobutyric acid, which catalyst contains P and Mo and exhibits reduced activity, with a gas containing a nitrogen-containing heterocyclic compound.

2. A process for producing methacrylic acid through catalytic vapor-phase oxidation of methacrolein or catalytic vapor-phase oxidative dehydrogenation of isobutyric acid, characterized by using a catalyst which has been reactivated by a method comprising treating a catalyst which has been gradually deteriorated during a long-term continuous reaction operation for use in methacrylic acid production by vapor-phase oxidation of methacrolein or vapor phase oxidative dehydrogenation of isobutyric acid, which catalyst contains P and Mo and exhibits reduced activity, with a gas containing a nitrogen-containing heterocyclic compound and steam; or with a gas containing a nitrogen-containing heterocyclic compound and a steam containing gas.

3. A process for producing methacrylic acid through catalytic vapor-phase oxidation of methacrolein or catalytic vapor-phase oxidative dehydrogenation of isobutyric acid, characterized by using a catalyst which has been reactivated by a method comprising treating a catalyst which has been gradually deteriorated during a long-term continuous reaction operation for use in methacrylic acid production by vapor-phase oxidation of methacrolein or vapor-phase oxidative dehydrogenation of isobutyric acid, which catalyst contains P and Mo and exhibits reduced activity, with a gas containing a nitrogen-containing heterocyclic compound, wherein the nitrogen-containing heterocyclic compound is at least one compound selected from pyridine, piperidine, piperazine, quinoline and derivatives thereof.

4. A process for producing methacrylic acid through catalytic vapor-phase oxidation of methacrolein or catalytic vapor-phase oxidative dehydrogenation of isobutyric acid, characterized by using a catalyst which has been reactivated by a method comprising treating a catalyst which has been gradually deteriorated during a long-term continuous reaction operation for use in methacrylic acid production by vapor-phase oxidation of methacrolein or vapor phase oxidative dehydrogenation of isobutyric acid, which catalyst contains P and Mo and exhibits reduced activity, with a gas containing a nitrogen-containing heterocyclic compound and steam; or with a gas containing a nitrogen-containing heterocyclic compound and a steam containing gas, wherein the nitrogen-containing heterocyclic compound is at least one compound selected from pyridine, piperidine, piperazine, quinoline and derivatives thereof.

5. The process for producing methacrylic acid through catalytic vapor-phase oxidation of methacrolein or catalytic vapor-phase oxidative dehydrogenation of isobutyric acid according to any one of claims 1 and 2–4 wherein the reactivation treatment is conducted within reaction tubes.

* * * * *